United States Patent [19]

Anderson

[11] Patent Number: 4,649,118
[45] Date of Patent: Mar. 10, 1987

[54] CELL CULTURING APPARATUS WITH IMPROVED STIRRING AND FILTER MEANS

[75] Inventor: John A. Anderson, Walden, N.Y.

[73] Assignee: The VirTis Company, Inc., Gardiner, N.Y.

[21] Appl. No.: 597,161

[22] Filed: Apr. 5, 1984

[51] Int. Cl.⁴ .............................................. C12M 1/02
[52] U.S. Cl. ..................................... 435/316; 435/286; 435/285; 435/284; 435/311; 366/255; 366/274
[58] Field of Search ....................... 366/255, 273, 274; 435/284–286, 299, 311, 316

[56] References Cited

U.S. PATENT DOCUMENTS

| | | | |
|---|---|---|---|
| 3,900,186 | 8/1975 | Balas | 366/248 X |
| 4,166,768 | 9/1979 | Tolbert et al. | 435/286 |
| 4,382,685 | 5/1983 | Pearson | 366/241 |
| 4,596,779 | 6/1986 | Ono | 435/286 |

FOREIGN PATENT DOCUMENTS 1080086  8/1967  United Kingdom ............... 366/128

Primary Examiner—Samuel Scott
Assistant Examiner—Allen J. Flanigan
Attorney, Agent, or Firm—Leydig, Voit & Mayer

[57] ABSTRACT

A cell culturing apparatus having a unitary filter and stirring head suspended within a culture vessel by a flexible conduit which permits movement of the head in a predetermined nonrotary path for stirring the culture medium within the vessel while at the same time permitting filtering and removal of expended medium and culture byproducts by passage through the head and flexible conduit. The flexible conduit has an upper portion fixedly secured to the culture vessel so as to eliminate the necessity for rotary bearings and the like between relative moving parts, and the head carries a magnet which is movable by means of a magnetic drive located outside the culture vessel. In one embodiment, an auxiliary supply line is disposed within the flexible conduit and head to permit the introduction of fluids into the culture vessel simultaneously with the removal of expended medium therefrom.

22 Claims, 4 Drawing Figures

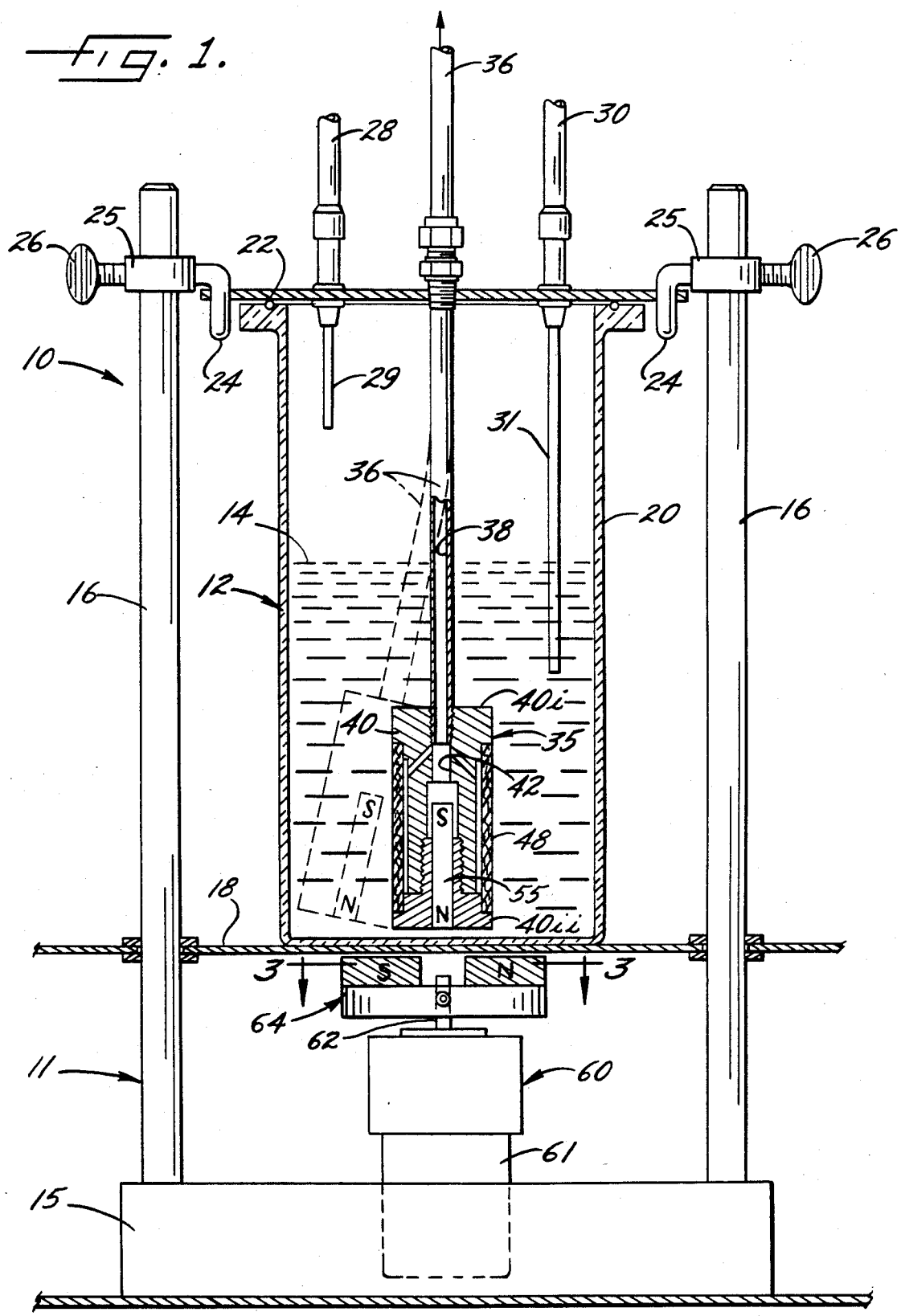

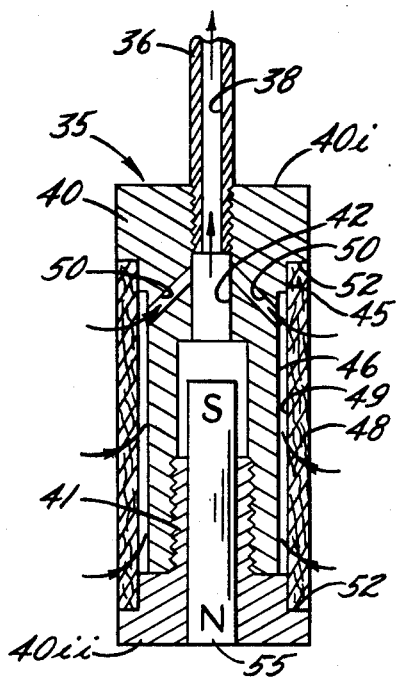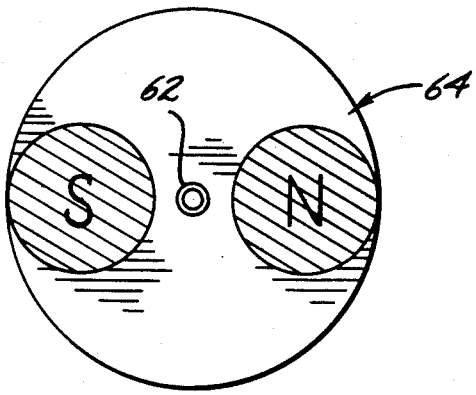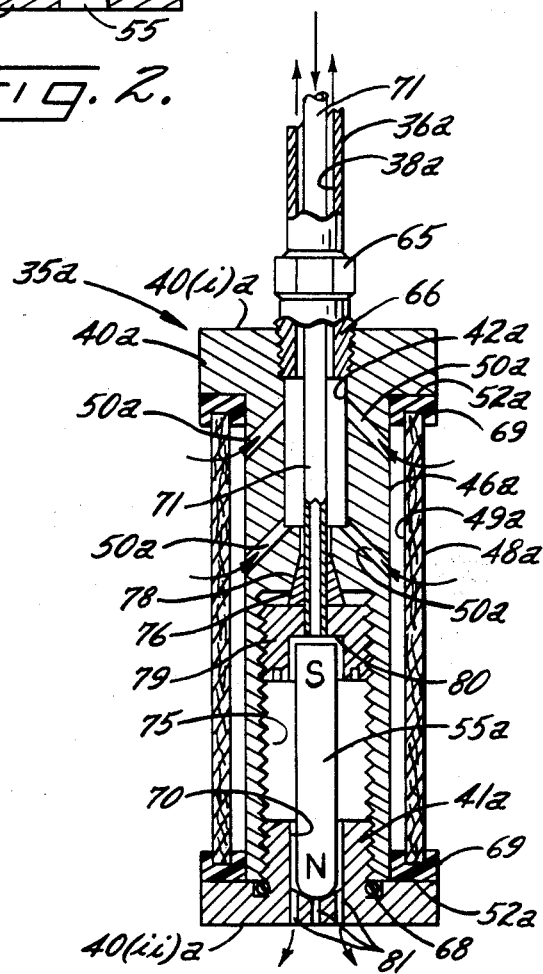

CELL CULTURING APPARATUS WITH IMPROVED STIRRING AND FILTER MEANS

DESCRIPTION OF THE INVENTION

The present invention relates to the processing and handling of cell cultures, and more particularly, to an apparatus for maintaining cells in suspension in a nutrient medium and for continuously removing expended medium from the cells to facilitate cell growth and concentration.

In the continuous culturing of cells, it is customary to introduce selected forms of live cells into a nutrient medium contained within a culture flask and to increase the cell concentration by maintaining the cells in suspension, while expended medium is removed from the flask and fresh medium introduced on a continuous or periodic basis. For this purpose, it is known to suspend a cylindrical rotatable filter in the flask by means of a tubular support rod and to continuously remove medium from the flask by drawing the medium through the filter and support rod. The filter serves to retain the cells within the flask to permit further cultivation and concentration, while allowing the removal of expended medium and culture byproducts for disposal, analysis, or other use. To prevent clogging of the filter through the built up cells about the outer periphery thereof, and to provide at least some stirring of the medium, it is known to rotate or spin the cylindrical filter by means of a magnetic drive. Such a cell culturing apparatus is shown in U.S. Pat. No. 3,172,235.

Cell culturing equipment of the foregoing type, however, has suffered from various drawbacks. Since the filter is rotated relative to the vessel within which it is supported, rotary seals and bearings are required between relative moving parts. Such seals and bearings have been difficult to establish and maintain, and in the event of failure or leakage, can interrupt the continuous operation of the apparatus or contaminate the products of the culture process. Moreover, rotary spinning of the filter alone sometimes is not adequate to maintain the cells in suspension for optimum cell growth. While auxiliary agitating devices have been employed to augment mixing of the medium, because many forms of cells in culture processing are relatively fragile and sensitive, the more strenuous agitation of the medium by such devices has sometimes resulted in cell damage.

It is an object of the present invention to provide an improved apparatus for processing and concentrating cells under sterile, controlled conditions.

Another object of the invention is to provide a cell culturing apparatus with a suspended filter which is adapted to effectively prevent the undesirable build up of cells about the periphery of the filter during use without the necessity for rotating or spinning the filter, and thus, without the need for rotary seals and bearings between relative moving parts.

A further object is to provide a cell culturing apparatus as characterized above which effects gentle, effective stirring of the culture medium for maintaining cell suspension for optimum growth and concentration.

Still another object is to provide a cell culturing apparatus of the foregoing type which permits both the removal of expended medium and the introduction of fresh medium or sparging air through a unitary filter mechanism, thus minimizing the number of penetrations into the culture flask.

Yet another object is to provide such a cell culturing apparatus which is of relatively simple construction, and thus, is adapted for economical manufacture and easy and reliable use.

Other objects and advantages of the invention will become apparent upon reading the following detailed description and upon reference to the drawings, in which:

FIG. 1 is a side elevation view, in partial section, of an illustrated cell culturing apparatus embodying the present invention;

FIG. 2 is an enlarged vertical section of the filter and stirring head of the apparatus shown in FIG. 1;

FIG. 3 is a horizontal section of the magnetic drive of the illustrated apparatus, taken in the plane of line 3—3 in FIG. 1; and FIG. 4 is an vertical section of an alternative form of filter and stirring head for use with the apparatus of the present invention.

While the invention is susceptible of various modifications and alternative constructions, certain preferred embodiments have been shown in the drawings and will be described below in detail. It should be understood, however, that there is no intention to limit the invention to the specific forms described but, on the contrary, the intention is to cover all modifications, alternative constructions and equivalents falling within the scope of the invention.

Referring now more particularly to FIG. 1 of the drawings, there is shown an illustrated cell culturing apparatus 10 embodying the present invention. The apparatus 10 includes a base 11 that supports a liquid-tight culture vessel 12 containing a determined quantity of a culture medium 14 into which a known cell form may be introduced for growth and concentration under controlled conditions. It will be understood that use of the term "cell" herein is intended to encompass microorganisms or cells derived from tissues of higher organisms, whether plant or animal, and the cell culturing apparatus of the present invention may be utilized for a wide variety of medical, laboratory, or commercial uses including the production of pharmaceuticals, alcohol, alcoholic beverages, as well as other applications in which it is necessary to analyze cells produced in a controlled culture environment or byproducts therefrom.

In the illustrated apparatus 10, the base 11 includes a lowermost platform 15 with a plurality of upstanding support rods 16 which carry a base plate 18, preferably made of plastic, for supporting the culture vessel 12. The culture vessel 12 comprises a culture flask 20 and a lid or closure plate 21 enclosing the upper end of the flask 20. An O-ring seal 22 is interposed between the lid 21 and flask 20 for maintaining the desired sterile environment within the flask. For retaining the lid 21 in assembled position on the flask 20, clamps 24 are rotatably mounted in carriers 25 fixed at the desired height on the support rods 16. The clamps 24 each have a gripping flange 26 that permits rotation of the clamp 24 between a downwardly directed condition, as illustrated in FIG. 1, retaining the lid 21 in assembled condition on the flask 20 and a raised condition that allows removal and replacement of the lid 21.

To permit the supply of fresh liquid medium into the sealed culture vessel 12, a liquid supply conduit 28 in this instance is coupled to a liquid feed tube or penetration 29 mounted in sealed relation in the lid 21 in a known manner. For permitting the withdrawal of the medium and suspended cells, or samples thereof, a conduit 30 is coupled to a tubular penetration 31, also mounted in sealed relation in the lid 21, but with a lower end extending below the level of the medium 14 in the vessel. It will be understood that additional penetrations may be mounted in the lid 21, such as for the supply of chemical agents and for the introduction and removal of gases. The number and use of such penetrations, of course, will depend upon the particular use of the apparatus and the culture process that is to be carried out. Appropriate means also may be provided for controlling and maintaining the temperature and pressure of the environment within the culture vessel.

In accordance with the invention, non-rotatable, unitary filter and stirring means is provided for effecting relatively gentle stirring of the culture medium and removal of spent medium and culture byproducts for optimum cell growth and concentration, without the necessity for undesirable rotary bearings and seals between moving parts and without the need for auxiliary agitators. To this end, the apparatus 10 includes a filter head 35 which is supported within the culture vessel 12 for swinging movement at the end of a flexible tubular member 36 fixedly held in the lid 21. The tubular member 36 preferably is made of plastic, such as teflon, and is sufficiently flexible to permit swinging movement of the filter head 35 in the medium 14, while at the same time having sufficient rigidity to prevent collapse of the tubular member and blockage of an internal passageway 38 therein. For fixedly supporting the tubular member in the vessel lid 21, a clamp fitting 39 is mounted in threaded engagement with the lid and is adapted to positively engage and hold the tubular member 36 at a selected location for establishing the desired position of the filter head 35 in the vessel 12.

The illustrated filter head 35 includes a generally cylindrical filter block 40 in this instance comprising an upper block portion 40(*i*) and a lower block portion 40(*ii*), the latter being formed with an upstanding extension 41 threadedly engaging a central internally threaded recess in the underside of the upper block portion 40(*i*). The filter block 40 is formed with a central bore 42, the upper end of which is in threaded engagement with a lowermost end of the tubular member 36 so as to communicate with the tubular member passageway 38. The filter block 40 is further formed with an outer peripheral recess 45 and an inner peripheral recess 46, the latter having a length slightly shorter than the outer peripheral recess 45 such that the outer recess 45 defines seats at opposed ends for an annular filter 48 and the inner recess 46 defines a small annular space or passageway 49 adjacent the inside surface of the filter 48. A plurality of transverse passages 50 in this instance communicate between an upper end of the annular passage 49 and the central bore 42 of the filter block 40. The filter block 40 preferably is made of a rigid plastic material, such as teflon, so as to be relatively light in weight, permit easy machining or molding of the recesses and passages therein, and be susceptible to use in applications such as radioactive fermentation which preclude exposure of metals. The filter 48 may be of a commercially known type, preferably being formed of a rigid screen covered by an outer mesh, membrane, fabric or the like having a desired pore or opening size for the culture process that is to be carried out. The filter 48 is assembled in tight fitting relation on the seats defined by the outer peripheral recess 45, and is positively held in place between opposed shoulders 52 of the upper and lower block portions 40(*i*), 40(*ii*). Hence, to effect removal and replacement of the filter 48, the lower filter block portion 40(*ii*) may be unscrewed and removed from the upper block portion 40(*i*).

In carrying out the invention, magnetic drive means is provided for moving the filter head 35 through the medium in swinging fashion on the end of said tubular support member 36 for creating shear forces about the periphery of the filter 48 to prevent the undesirable build up and clogging of cells on the outer periphery of the filter and to effect relatively gentle stirring of the medium 14 for maintaining the cells in suspension for optimum growth and concentration without cell damage. To this end, the lower block portion 40(*ii*) carries a magnet 55 which preferably is press fit in a central bore therein. The magnet 55 in this instance is supported in vertical fashion with the north pole thereof at a lower end and the south pole at the upper end.

For effecting swinging movement of the filter head 35, a magnetic drive motor 60 is mounted in close relation to the underside of the vessel 12 (FIG. 1). The magnetic drive motor 60 includes an electric motor 61 supported in the platform 15 with its output shaft 62 upwardly extending. A drive magnet 64 is mounted on the shaft 62 for rotation in a horizontal plane in closely spaced relation to the support plate 18 upon which the culture vessel 12 is mounted. By virtue of such arrangement, the north pole of the filter head magnet 55 will be attracted to the magnetic field of the south pole of the drive motor magnet 64 and upon rotation of the drive magnet 64 will follow the south pole in a generally circular path. By controlling the speed of the drive motor 61, the speed of movement of the filter head 35 may be controlled to effect the desired stirring action without cell injury, while at the same time maintaining the filter 48 free from cell build up.

In operation of the cell culturing apparatus 10, after initial charging of the culture vessel 12 with liquid medium 14 and the desired cell form, the sealed vessel 12 may be maintained at the desired temperature and atmospheric conditions for the culture process to be carried out. Expended medium or filtrate may be continuously or periodically removed from the culture vessel 12 by drawing the medium 14 through the filter head 35, causing it to pass through the filter 48, the annular and transverse passages 49, 50, the central bore 42, and out the tubular member passageway 38. Fresh liquid medium in this case may be introduced through the conduit 28 and penetration tube 29. At the same time, by actuation of the drive motor 61, the filter head 35 may be moved in swinging fashion at the end of the flexible tubular member 36 to effect desired stirring of the liquid medium for optimum cell growth and concentration. Since the tubular member 36 remains fixedly secured to the culture vessel 12, such stirring and filtering may be effected without the need for rotary seals and bearings, which heretofore have created leakage and maintenance problems. It will be appreciated that the liquid medium 14 may be directed through the filter head 35 and tubular member 36 by pressurizing the contents of the culture vessel 12 and allowing this pressure to force the liquid through the filter and out the tubular member, or alternatively, by applying a vacuum pressure to the tubular member, such as through a vacuum pump. It will also be understood that in leu of the magnetic drive motor 60, alternate means may be provided for moving magnetic fields in close relation to the filter head magnet 55 for effecting the desired path of travel of the filter head through the liquid medium.

Referring now to FIG. 4, there is shown an alternative form of filter head 35a and flexible tubular support member 36a, wherein items similar to those described above have been given similar reference numerals with the distinguishing suffix "a". In this instance, the filter head 35a is fixed to the flexible tubular member 36a by means of a bushing 65 mounted at the end of the tubular member 36a with a threaded end 66 engaging an upper threaded portion of a central bore 42a of the filter head. The filter head 35a again comprises an upper block portion 40(i)a and a lower block portion 40(ii)a, with an upstanding extension 41a threadedly engaging a central internally threaded bore of the upper block portion 40(i)a. An O-ring seal 68 is interposed between the upper and lower filter block portions 40(i)a, 40(ii)a. A cylindrical filter 48a in this case is supported between opposed annular bushings 69, which in turn are retained between annular shoulders 52a of the filter block portions such that a small annular space or passage 49a exists between an annular recess 46a and the inside wall of the filter 48a. Transverse passages 50a communicate between the annular passage 49a and the central bore 42a for permitting liquid medium to be drawn through the filter 48, the passages 49a, 50a, central bore 42a, and through the flexible tubular member 36 on a continuous or periodic basis, in the manner previously described. For effecting swinging movement filter head 35a by means of a magnetic drive as previously described, a magnet 55a is loosely supported in a cradle recess 70 formed in the lower filter block portion 40(ii)a.

In accordance with a further aspect of the invention, the filter head 35a and flexible tubular support 36a include means for permitting the simultaneous introduction of fresh medium, or other liquids or gases, into the sealed culture vessel with which it is used. For this purpose, an auxiliary supply line 71 is carried within the flexible tubular member 36a and filter head 35a such that liquid or gas may be directed through the auxiliary supply line 71 and filter head 35a into the culture vessel, as shown by the arrows in FIG. 4, at the same time filtrate is being directed outwardly through the tubular member 36a in a space or passage 38a defined between the outer periphery of the auxiliary line 71 and the inner peripheral wall of the tubular member 36a. In the illustrated embodiment, the auxiliary supply line 71 extends through the tubular member 36a, the central bore 42a of the filter block 40a and into communication with a chamber 75 formed in the lower end of the filter block 40. For sealing the central bore 42a from the lower chamber 75 and for positively securing the lower end of the auxiliary line 71 in the filter block 40, a ferrule clamp 76 is disposed about a lower portion of the auxiliary line 71 and is forced into sealing engagement with the auxiliary line 71 and a tapered seat 78 in the filter block portion 40(i)a by means of a ferrule clamp nut 79 that is threadedly advanced upwardly in the chamber 75 which is internally threaded for such purpose. The clamp nut 79 is formed with a socket recess 80 within which the upper end of the magnet 55a is loosely disposed.

It will be seen that when the filter head 35a is utilized in the culture vessel in the manner previously described, as expended liquid medium is drawn through the filter 48a, the annular and transverse passages 49a, 50a, the central bore 42a, and outward through the flexible tubular member passage 38a, fresh nutrient medium, chemicals, sparging air, or the like, may be simultaneously introduced through the auxiliary line 71, which exits and flows about the magnet 55a, through the chamber 75 and through discharge slots 81 formed in the bottom of the lower filter block portion 40(ii)a. The ferrule clamp 78 forms a fixed seal isolating the flow paths of the incoming and outgoing fluids. Since the auxiliary line 71 is supported entirely within the tubular member 36a and filter head 35a, the filter head 35a may be moved in the manner previously described by a magnetic drive without the necessity for rotary seals or the like between the tubular support member 36a and the vessel in which it is supported. It will be appreciated that such arrangement also minimizes the number of individual penetrations that must be provided in the culture vessel.

From the foregoing, it can be seen that the unitary filter and stirring head of the cell culturing apparatus of the present invention is adapted to effectively stir culture mediums in an easily controlled and relatively gentle fashion, while simultaneously filtering and withdrawing expended medium and culture byproducts, as well as permitting the introduction of fresh medium or sparging air, all without the necessity for supporting the filter head in rotary bearings or the like which heretofore have created maintenance and leakage problems. The apparatus lends itself to versatile and reliable use, while being relatively simple in construction, and thus, economical to manufacture. It will be further appreciated that since the filter head and tubular support may be formed of nonmetallic parts, the apparatus may be used for radioactive fermenters and other applications which preclude metal exposure.

I claim as my invention:

1. An apparatus for culturing cells in a liquid medium comprising
   a fluid tight culture vessel for containing a quantity of said medium and cells,
   a filter head disposed within said vessel and having a filter media with openings smaller than the cells to be cultured,
   flexible conduit means having one end fixed in fluid communication with said filter head for permitting liquid medium in said vessel to be drawn through said filter head and directed out of said vessel by passage through said flexible conduit means,
   means fixedly supporting a portion of said flexible conduit means to said vessel,
   magnetic means carried by said filter head, and
   magnetic drive means located outside said vessel for moving a magnetic field in close relation to said filter head magnetic means for moving said filter head and the end of said flexible conduit means fixed thereto in said vessel for stirring the liquid medium and cells therein without relative movement between said vessel and the fixed portion of said flexible conduit means.

2. The cell culturing apparatus of claim 1 in which said filter head is supported by said flexible conduit means in spaced relation of the bottom of said vessel.

3. The cell culturing apparatus of claim 1 in which said vessel includes a closure lid, and said fixed flexible conduit portion is secured to said lid with said filter head suspended by said flexible conduit means.

4. The cell culturing apparatus of claim 1 in which said magnetic drive means is a motor having a drive magnet disposed in close relation to the underside of said vessel.

5. The cell culturing apparatus of claim 4 in which said drive magnet is rotatably driven by said motor for moving said filter head in the generally circular stirring path of travel within said vessel.

6. The cell culturing apparatus of claim 5 in which said filter head magnetic means is a magnet vertically supported in said filter head with one pole of said magnet in close relation to the bottom of said vessel and the other pole of said magnet disposed a greater distance from the bottom of said vessel, and said drive magnet is mounted for rotatable movement in a horizontal plane in closely spaced relation to the bottom of said vessel.

7. The cell culturing apparatus of claim 1 in which said filter head includes a filter block, said filter media being disposed about the periphery of said filter block, and said filter block being formed with passages communicating between said filter media and said flexible conduit means.

8. The cell culturing apparatus of claim 7 in which said magnetic means is a magnet disposed within said filter block.

9. The cell culturing apparatus of claim 8 in which said magnet is supported in vertically disposed relation in said filter block and has one pole adjacent the lower end of said block.

10. The cell culturing apparatus of claim 7 in which said filter block comprises upper and lower block portions assembled in releasable engagement for positively supporting and retaining said filter media.

11. The cell culturing apparatus of claim 10 in which said block portions define a cylindrical peripheral recess within which said filter media is retained.

12. An apparatus for culturing cells in a liquid medium comprising
a fuild tight culture vessel for containing a quantity of said medium and cells,
a filter head disposed within said vessel and having a filter media with openings smaller than the cells to be cultured,
flexible conduit means having one end fixed in fluid communication with said filter head for permitting liquid medium in said vessel to be drawn through said filter head and directed out of said vessel by passage through said flexible conduit means,
means fixedly supporting a portion of said flexible conduit means to said vessel,
magnetic means carried by said filter head,
magnetic drive means located outside said vessel for moving a magnetic field in close relation to said filter head magnetic means for moving said filter head and the end of said flexible conduit means fixed thereto in said vessel for stirring the liquid medium and cells therein without relative movement between said vessel and the fixed portion of said flexible conduit means, and
means disposed within said flexible conduit means for permitting the introduction of fluids into said vessel simultaneously with drawing of said liquid medium through said filter head and directing it through said flexible conduit means.

13. The cell culturing apparatus of claim 12 in which said fluid introducing means inside said flexible conduit means includes an auxiliary supply line disposed within said flexible conduit means and having a discharge end communicating with said filter head, said filter head being formed with passage means communicating between the discharge end of said auxiliary supply line and the interior of said vessel without passage through said filter media.

14. The cell culturing apparatus of claim 13 in which said filter head includes first passage means communicating between said filter media and said flexible conduit means, and second passage means communicating between said auxiliary supply line discharge end and the interior of said vessel.

15. The cell culturing apparatus of claim 14 including fixed means securing a discharge end of said auxiliary supply line to said filter head and sealing said first passage means from said second passage means.

16. The cell culturing apparatus of claim 1 in which said flexible conduit means and filter head are made of a thermoplastic material.

17. The cell culturing apparatus of claim 16 in which said flexible conduit means and filter head are made of teflon.

18. An apparatus for culturing cells in a liquid medium comprising
a fluid tight culture vessel for containing a quantity of said medium and cells,
a stirring head,
flexible conduit means suspending said stirring head within said vessel and having one end fixed in fluid communication with said stirring head for permitting liquid medium in said vessel to be drawn through said filter head and directed out of said vessel by passage through said flexible conduit means,
means fixedly securing a portion of said flexible conduit means to said vessel,
magnetic means carried by said stirring head, and
magnetic drive means located outside said vessel for moving a magnetic field in close relation to said stirring head magnetic means for moving said stirring head within said vessel for stirring the liquid medium and cells therein without relative movement between said vessel and said fixed portion of said flexible conduit means.

19. The cell culturing apparatus of claim 18 in which said magnetic drive means is a motor having a drive magnet disposed in close relation to the underside of said vessel.

20. The cell culturing apparatus of claim 19 in which said drive magnet is rotatably driven by said motor for moving said stirring head in a generally circular stirring path of travel within said vessel.

21. The cell culturing apparatus of claim 20 in which said stirring head magnetic means is a magnet vertically supported in said stirring head with one pole of said magnet in close relation to the bottom of said vessel and the other pole of said magnet disposed a greater distance from the bottom of said vessel, and said drive magnet is mounted for rotatable movement in a horizontal plane in closely spaced relation to the bottom of said vessel.

22. The cell culturing apparatus of claim 18 in which said stirring head comprises a block and filter media disposed about the outer periphery of said block, and said block being formed with passage means communicating between said filter media and said flexible conduit means so as to permit liquid medium in said vessel to be drawn through said filter media and block and directed out said vessel by passage through said flexible conduit means.

* * * * *